US009720004B2

(12) United States Patent
Singh et al.

(10) Patent No.: US 9,720,004 B2
(45) Date of Patent: Aug. 1, 2017

(54) IMMUNOASSAYS EMPLOYING NON-PARTICULATE CHEMILUMINESCENT REAGENT

(71) Applicant: Siemens Healthcare Diagnostics Inc., Tarrytown, NY (US)

(72) Inventors: Pratap Singh, Wilmington, DE (US); Yi Feng Zheng, Wilmington, DE (US); Liping Geng, Newark, DE (US); Roland Janzen, Hockessin, DE (US); Carsten Schelp, Marburg (DE)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 0 days.

(21) Appl. No.: 15/131,120

(22) Filed: Apr. 18, 2016

(65) Prior Publication Data

US 2016/0231336 A1   Aug. 11, 2016

Related U.S. Application Data

(62) Division of application No. 12/403,299, filed on Mar. 12, 2009, now Pat. No. 9,347,947.

(51) Int. Cl.
*G01N 33/78* (2006.01)
*G01N 33/58* (2006.01)

(52) U.S. Cl.
CPC .......... *G01N 33/78* (2013.01); *G01N 33/582* (2013.01); *G01N 2333/59* (2013.01)

(58) Field of Classification Search
CPC ... G01N 33/78; G01N 33/582; G01N 2333/59
See application file for complete search history.

(56) References Cited

U.S. PATENT DOCUMENTS

| 3,817,837 A | 6/1974 | Rubenstein et al. |
| 3,996,345 A | 12/1976 | Ullman et al. |
| 4,199,559 A | 4/1980 | Ullman et al. |
| 4,261,968 A | 4/1981 | Ullman et al. |
| 5,545,834 A | 8/1996 | Singh et al. |
| 5,578,498 A | 11/1996 | Singh et al. |
| 5,709,994 A | 1/1998 | Pease et al. |
| 5,811,311 A | 9/1998 | Singh et al. |
| 5,902,606 A | 5/1999 | Wunderlich et al. |
| 6,124,103 A | 9/2000 | Bose |
| 6,143,514 A | 11/2000 | Ullman et al. |
| 6,180,354 B1 | 1/2001 | Singh et al. |
| 6,251,581 B1 | 6/2001 | Ullman et al. |
| 6,340,599 B1 | 1/2002 | Singh et al. |
| 6,346,384 B1 | 2/2002 | Pollner |
| 6,406,667 B1 | 6/2002 | Singh et al. |
| 6,531,278 B1 | 3/2003 | Weimer |
| 6,573,054 B2 | 6/2003 | Patel et al. |
| 6,692,975 B2 | 2/2004 | Singh et al. |
| 6,703,248 B1 | 3/2004 | Singh et al. |
| 6,783,947 B1 | 8/2004 | de Keczer et al. |
| 6,797,481 B1 | 9/2004 | Ullman et al. |
| 6,916,667 B2 | 7/2005 | Singh et al. |
| 7,022,529 B2 | 4/2006 | Singh et al. |
| 7,033,775 B2 | 4/2006 | Ullman et al. |
| 7,101,682 B2 | 9/2006 | Ullman et al. |
| 7,229,842 B2 | 6/2007 | Singh et al. |
| 7,255,998 B1 | 8/2007 | Tashiro et al. |
| 2001/0014450 A1 | 8/2001 | Lishanski et al. |
| 2002/0058280 A1 | 5/2002 | Singh et al. |
| 2003/0118595 A1 | 6/2003 | Niemeyer et al. |
| 2004/0121490 A1 | 6/2004 | Singh et al. |
| 2004/0175696 A1 | 9/2004 | Ullman et al. |
| 2004/0241711 A1 | 12/2004 | Singh et al. |
| 2004/0253657 A1 | 12/2004 | Ullman et al. |
| 2005/0214875 A1 | 9/2005 | Singh et al. |
| 2006/0063219 A1 | 3/2006 | Kuo et al. |
| 2006/0099664 A1 | 5/2006 | Ullman et al. |
| 2006/0121506 A1 | 6/2006 | Singh et al. |
| 2006/0239965 A1 | 10/2006 | Szoka et al. |
| 2006/0270063 A1 | 11/2006 | Craig et al. |
| 2007/0009964 A1 | 1/2007 | Soto-Jara et al. |
| 2007/0166778 A1 | 7/2007 | Jacq et al. |
| 2011/0014721 A1 | 1/2011 | Evangelista et al. |

FOREIGN PATENT DOCUMENTS

| CA | 2177143 | 6/1995 |
| CN | 1227532 | 3/2003 |

(Continued)

OTHER PUBLICATIONS

Wang, G. et al., Homogeneous Time-Resolved Fluoroimmunoassay of 3,5,3-Triiodo-I-Thyronine in Human Serum by Using Europhium Fluorescence Energy Transfer, Talanta 2006, vol. 70, No. 1, p. 133-138.

(Continued)

*Primary Examiner* — Gary W Counts

(74) *Attorney, Agent, or Firm* — Cynthia G. Tymeson

(57) ABSTRACT

Methods and reagents are disclosed for conducting assays. Embodiments of the present methods and reagents are concerned with chemiluminescent reagents for determining the presence and/or amount of an analyte in a sample suspected of containing the analyte. The reagent is non-particulate and comprises a binding partner for the analyte and a chemiluminescent composition comprising an olefinic compound and a metal chelate. In embodiments of an assay, a combination is provided that comprises a sample suspected of containing the analyte, a chemiluminescent reagent as described above and a sensitizer reagent capable of generating singlet oxygen. The combination is subjected to conditions for binding of the analyte to the binding partner for the analyte. The sensitizer is activated and the amount of luminescence generated by the chemiluminescent composition is detected wherein the amount of luminescence is related to the amount of the analyte in the sample.

17 Claims, 3 Drawing Sheets

(56) References Cited

FOREIGN PATENT DOCUMENTS

JP  4134304  5/1992
RU  2213974 C1  10/2003

OTHER PUBLICATIONS

Yuan, J. et al., Highly Sensitive Time-Resolved Fluoroimmunoassay of Human Immunoglobulin in E by Using a New Europhium Fluorescent Chelate as a Label, Analytical Biochemistry 1997, vol. 254, No. 2, p. 283-287.

Antibody-BSA-Thioxene-Complex

| Sample Id | kcounts | mIU/L | Mean | SD | CV |
|---|---|---|---|---|---|
| 6BD036 Level A | 0.10 | -0.05 | 0.00 | 0.13 | N/A |
| | 0.13 | 0.14 | | | |
| | 0.09 | -0.10 | | | |
| 6BD036 Level B | 0.24 | 1.02 | 0.98 | 0.05 | 4.89 |
| | 0.24 | 0.98 | | | |
| | 0.23 | 0.93 | | | |
| 6BD036 Level C | 0.67 | 4.06 | 3.89 | 0.24 | 6.26 |
| | 0.66 | 3.99 | | | |
| | 0.60 | 3.61 | | | |
| 6BD036 Level D | 2.55 | 17.00 | 17.07 | 0.18 | 1.07 |
| | 2.54 | 16.94 | | | |
| | 2.59 | 17.28 | | | |
| 6BD036 Level E | 6.26 | 45.50 | 46.32 | 1.45 | 3.12 |
| | 6.53 | 47.99 | | | |
| | 6.25 | 45.46 | | | |
| 6BD036 Level F | 10.77 | 98.06 | 96.43 | 3.61 | 3.74 |
| | 10.40 | 92.29 | | | |
| | 10.83 | 98.93 | | | |

# IMMUNOASSAYS EMPLOYING NON-PARTICULATE CHEMILUMINESCENT REAGENT

This application is a Division of U.S. Ser. No. 12/403,299 filed Mar. 12, 2009, now U.S. Pat. No. 9,347,947.

BACKGROUND

This invention relates to reagents, which are capable of generating signal, for use in methods, compositions and kits for determining an analyte in a sample.

The clinical diagnostic field has seen a broad expansion in recent years, both as to the variety of materials of interest that may be readily and accurately determined, as well as the methods for the determination. Most methods involve generation of a signal in relation to the presence and/or amount of one or more analytes in a sample. Luminescent compounds, such as fluorescent compounds and chemiluminescent compounds, find wide application in the assay field because of their ability to emit light. Particles, such as latex particles, liposomes and the like have been utilized in assays. Both absorptive dyes and dyes that impart fluorescent or chemiluminescent properties have been incorporated into particles. In one particular approach, particles that comprise one or more metal chelates such as, for example, lanthanide chelates, are employed for generating a signal.

An induced luminescence immunoassay is described in U.S. Pat. Nos. 5,340,716 and 6,251,581, which disclosures are incorporated herein by reference. In one approach the assay uses a particle incorporating a photosensitizer and a label particle incorporating a chemiluminescent compound. The label particle is conjugated to a binding partner that is capable of binding to an analyte to form a complex, or to another moiety to form a complex in relation to the presence of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of analyte present. In one particular approach, the chemiluminescent particles comprise one or more metal chelates such as, for example, lanthanide chelates.

In a variation of the induced luminescence method, a particulate support is employed that comprises both (a) a photosensitizer capable upon irradiation of generating singlet oxygen and (b) a chemiluminescent compound capable of being activated by singlet oxygen. The methods allow for generating delayed luminescence, which can be realized upon irradiation of the support. The methods have application to the determination of an analyte in a medium suspected of containing the analyte. One method comprises subjecting a medium suspected of containing an analyte to conditions under which a complex of binding partners is formed in relation to the presence of the analyte and determining whether the complex has formed by employing as a label a particulate composition having both chemiluminescent and photosensitizer properties. Upon activation of the photosensitizer property, singlet oxygen is generated and activates the chemiluminescent property. Such compositions and methods are described in U.S. Pat. No. 5,709,994, the relevant disclosure of which is incorporated herein by reference.

SUMMARY

One embodiment of the present invention is a chemiluminescent reagent for determining the presence and/or amount of an analyte in a sample suspected of containing the analyte. The chemiluminescent reagent is non-particulate and comprises a binding partner for the analyte and a chemiluminescent composition comprising an olefinic compound and a metal chelate.

Another embodiment of the present invention is a method for determining the presence and/or amount of an analyte in a sample suspected of containing the analyte. A combination is provided that comprises the sample, a chemiluminescent reagent as described above and a sensitizer reagent capable of generating singlet oxygen. The combination is subjected to conditions for binding of the analyte to the binding partner for the analyte. The sensitizer is activated and the amount of luminescence generated by the chemiluminescent composition is detected wherein the amount of luminescence is related to the amount of the analyte in the sample.

DETAILED DESCRIPTION OF SPECIFIC EMBODIMENTS

General Discussion

Figure 1:
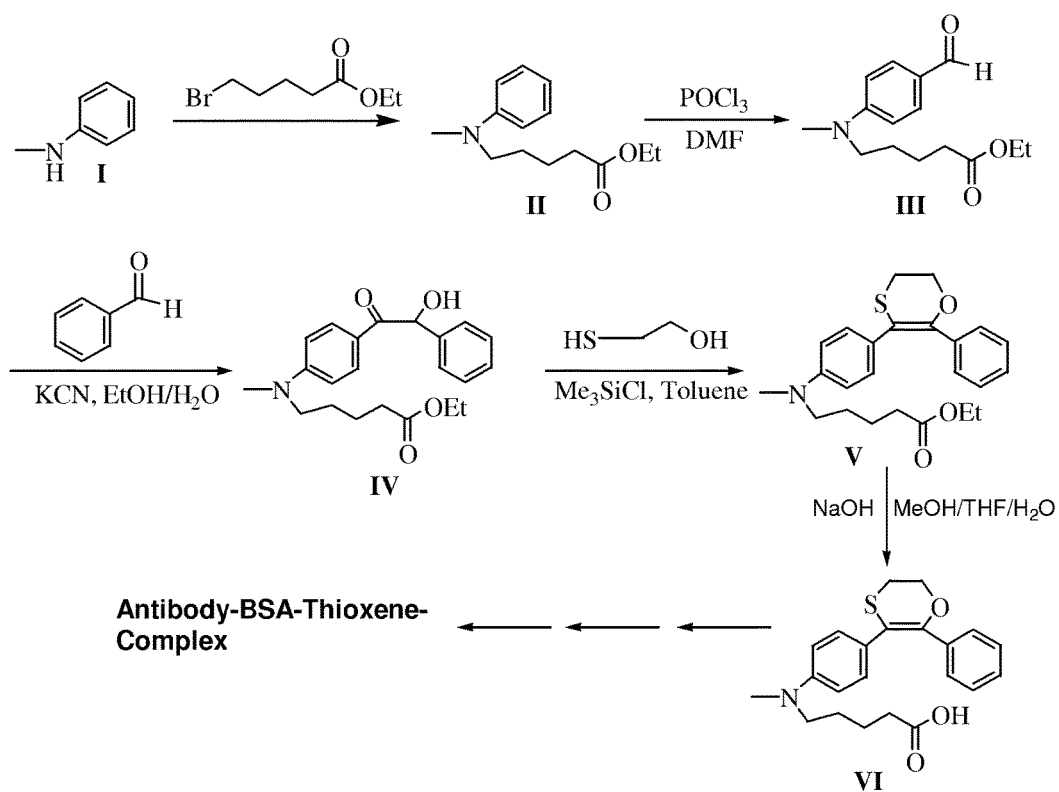
FIG. 1 is a depiction of a scheme for producing a chemiluminescent reagent in accordance with present embodiments.

Embodiments of the present methods and reagents are concerned with chemiluminescent reagents for determining the presence and/or amount of an analyte in a sample suspected of containing the analyte. The reagent is non-particulate and comprises a binding partner for the analyte and a chemiluminescent composition comprising an olefinic compound and a metal chelate. The chemiluminescent reagent in accordance with the present embodiments exhibits good solubility in an aqueous medium such as an aqueous assay medium. The non-particulate chemiluminescent reagent has enhanced stability for use in assays for detection of analytes; furthermore, the reagent exhibits good signal response to changes in the concentration of analyte. When used in an assay, the non-particulate chemiluminescent reagent in accordance with the present embodiments is soluble in aqueous assay media and provides maximized performance including accuracy and sensitivity as well as stability of signal produced.

Performance of a particular assay format at the low end of the medical decision range can be monitored by monitoring the difference in the amount of signal obtained for calibrators spanning the suspected concentration range of interest of the analyte. A large difference or separation between the signal for calibrators such as, for example, calibrator L1 and calibrator L2 or calibrator L2 and calibrator L3, is desired. For example, six calibrators may be employed, arbitrarily named L1-L6. Signal to noise ratio may be evaluated by determining an amount of signal using a calibrator that contains no analyte, arbitrarily designated calibrator L1 (background), and the amount of signal obtained for a calibrator containing a first known amount of analyte above zero, arbitrarily designated calibrator L2. This evaluation may also include determining an amount of signal using calibrator L1 and the amount of signal for a calibrator containing a second known amount of analyte above zero, arbitrarily designated L3. Such an evaluation may also include such determination using calibrators L4, L5, L6 and so forth. The embodiments discussed herein provide for better performance in an assay for an analyte compared to reagents not in accordance with the present embodiments.

A large difference between the signal for calibrators, e.g., calibrator L1 and calibrator L2, or calibrator L1 and calibrator L6, is desired. For good sensitivity in the medical decision range, the difference in the signal detected between calibrator L1 and calibrator L2 is at least about 50%, at least about 75%, at least about 90%, at least about 100%, at least about 125%, at least about 150%, at least about 175%, at least about 200%, at least about 225%, at least about 250%, at least about 275%, at least about 300%, at least about 325%, at least about 350%, at least about 375%, at least about 400%, at least about 425%, and so forth. In some embodiments the signal detected for calibrator L6 is at least about 10 times, at least about 20 times, at least about 30 times, at least about 40 times, at least about 50 times, at least about 60 times, at least about 70 times, at least about 80 times, at least about 90 times, at least about 100 times, greater than the signal detected for calibrator L1. Depending on the assay format, the difference in signal may be an increase in signal or a decrease in signal. Typically, the results of the assays using the calibrators are presented in a graph format wherein the amount of signal is plotted against the concentration of the calibrators. In accordance with embodiments of the present invention the slope of the line between calibrator L1 and calibrator L2 generally is steeper compared with results obtained with assay reagents not in accordance with the present embodiments. Furthermore, the slope of the line from calibrator L1 to calibrator L6 is usually steeper compared with results obtained with assay reagents not in accordance with the present embodiments.

As mentioned above, embodiments of the present chemiluminescent reagents are non-particulate. As such, the reagents are distinguished from those employed in the aforementioned known induced luminescence assays, which employ particulate chemiluminescent reagents. The present chemiluminescent reagents exhibit good solubility in aqueous media. In embodiments of the chemiluminescent reagents, a binding partner for the analyte is covalently or non-covalently bound to a chemiluminescent composition comprising an olefinic compound and a metal chelate.

The binding partner for the analyte may be covalently bound to the chemiluminescent composition by a bond. On the other hand, the binding partner for the analyte may be covalently bound to the chemiluminescent composition by a linking group. In some embodiments, the linking group is hydrophilic. The term "hydrophilic" or "hydrophilicity" refers to a moiety that is polar and thus prefers polar molecules and prefers polar solvents. Hydrophilic molecules have an affinity for other hydrophilic moieties compared to hydrophobic moieties. The degree of hydrophilicity is controlled by the number of heteroatoms in the linking group.

In some embodiments the linking group is a macromolecule and may be polymeric. The polymeric macromolecule is generally about 1 to about 10,000 monomer units or more in length, or about 10 to about 10,000 monomer units in length, or about 100 to about 10,000 monomer units in length, or about 500 to about 10,000 monomer units in length, or about 1,000 to about 10,000 monomer units in length, or about 2,000 to about 10,000 monomer units in length, or about 3,000 to about 10,000 monomer units in length, or about 5,000 to about 10,000 monomer units in length, or about 10 to about 8,000 monomer units in length, or about 100 to about 8,000 monomer units in length, or about 1,000 to about 8,000 monomer units in length, or about 100 to about 7,000 monomer units in length and the like. The number of monomer units depends on the number of atoms in the monomer unit chain, the composition of the monomer unit, and so forth.

The molecular weight of the polymeric macromolecule is at least about 2,000. The molecular weight may be about 2,000 to about 10,000,000 or more, or about 2,000 to about 8,000,000, or about 2,000 to about 6,000,000, or about 2,000 to about 5,000,000 or about 2,000 to about 4,000,000, or about 2,000 to about 3,000,000 or about 2,000 to about 2,000,000, or about 2,000 to about 1,000,000, or about 5,000 to about 10,000,000 or more, or about 5,000 to about 8,000,000, or about 5,000 to about 6,000,000, or about 5,000 to about 5,000,000 or about 5,000 to about 4,000,000, or about 5,000 to about 3,000,000 or about 5,000 to about 2,000,000, or about 5,000 to about 1,000,000, or about 10,000 to about 10,000,000 or more, or about 10,000 to about 8,000,000, or about 10,000 to about 6,000,000, or about 10,000 to about 5,000,000 or about 10,000 to about 4,000,000, or about 10,000 to about 3,000,000 or about 10,000 to about 2,000,000, or about 10,000 to about 1,000,000, and the like.

The polymeric macromolecule may be linear or branched or a combination thereof. A linear polymer comprises a linear chain of atoms and a branched polymer comprises a branched chain of atoms. Each atom of the linear chain may have one or more substituents in place of hydrogen. In some embodiments the polymer may be a copolymer comprising more than one type of monomer unit. The relationship of the different monomer units in the polymer may be alternating, random, periodic and the like and may also be in a block copolymer arrangement where blocks of repeating monomer units form the polymer chain.

In some embodiments one or more of the monomer units of the polymeric macromolecule comprise carbon atoms and one or more heteroatoms such as, for example, oxygen, sulfur, nitrogen, phosphorus, and the like. The monomer units may comprise about 2 to about 50 atoms or more, or 5 to about 50 atoms, or about 10 to about 50 atoms, or about 20 to about 50 atoms, or about 30 to about 50 atoms, or about 2 to about 40 atoms or more, or 5 to about 40 atoms, or about 10 to about 40 atoms, or about 20 to about 40 atoms, or about 30 to about 40 atoms, or about 2 to about 30 atoms or more, or 5 to about 30 atoms, or about 10 to about 30 atoms, or about 20 to about 30 atoms, not counting hydrogen and may comprise a chain of from 2 to about 30 atoms, or about 5 to about 30 atoms or more, or 10 to about 30 atoms, or about 15 to about 30 atoms, or about 20 to about 30 atoms, or about 2 to about 25 atoms or more, or 5 to about 25 atoms, or about 10 to about 25 atoms, or about 15 to about 25 atoms, or about 20 to about 25 atoms, or about 2 to about 20 atoms or more, or 5 to about 20 atoms, or about 10 to about 20 atoms, or about 15 to about 20 atoms, or about 2 to about 15 atoms, or about 5 to about 15 atoms, or about 10 to about 15 atoms, each independently selected from the group normally consisting of carbon, oxygen, sulfur, nitrogen, and phosphorous.

The number of heteroatoms in a monomer unit of the polymeric macromolecule may range from about 0 to about 20, or about 0 to about 15, or about 0 to about 10, or about 0 to about 5, or about 1 to about 20, or about 1 to about 15, or about 1 to about 10, or about 1 to about 5, or about 2 to about 20, or about 2 to about 15, or about 2 to about 10, or about 2 to about 5, or about 5 to about 20, or about 5 to about 15, or about 5 to about 10, and the like. In some embodiments, the number of heteroatoms is sufficient to render the linking group hydrophilic and enhance the solubility of the chemiluminescent reagent in accordance with the present embodiments. In this regard, the number of heteroatoms in the monomer unit of the polymeric macromolecule may range from about 1 to about 20, or about 1 to about 15, or about 1 to about 10, or about 1 to about 5, or about 2 to about 20, or about 2 to about 15, or about 2 to about 10, or about 2 to about 5, or about 5 to about 20, or about 5 to about 15, or about 5 to about 10, and the like. When heteroatoms are present, oxygen is normally present as oxo or oxy, bonded to carbon, sulfur, nitrogen or phosphorous, nitrogen is normally present as azo, cyano, isocyano, nitro, nitroso, amido or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid, or its nitrogen derivative or phosphoric acid derivative, are linked, amides, amidines and phosphoramides are formed respectively. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed.

In some embodiments, the linking group is not a macromolecule and has a molecular weight less than about 2000, or less than about 1500, or less than about 1000, or less than about 500, or the like. Such linking groups may comprise about 2 to about 200 atoms, or 4 to about 150 atoms, or about 5 to about 100 atoms, not counting hydrogen and may comprise a chain of from 2 to about 100 atoms, or 3 to about 90 atoms, or about 4 to about 80 atoms, or about 5 to about 70 atoms, or the like, each independently selected from the group normally consisting of carbon, oxygen, sulfur, nitrogen, and phosphorous. The number of heteroatoms in such linking groups is dependent on the size of the linking group and will normally range from about 0 to about 50, 1 to about 45, or about 2 to about 40. The heteroatoms may be in the forms indicated above in the discussion concerning macromolecular linking groups. In some embodiments, the number of heteroatoms is sufficient to render the linking group hydrophilic and enhance the solubility of the resultant composition in accordance with the present embodiments. In this regard, the number of heteroatoms in the linking group depends on the size of the linking group and may range from about 5 to about 50, or about 10 to about 50, or about 15 to about 50, or about 5 to about 40, or about 10 to about 40, or about 15 to about 40, or about 5 to about 30, or about 10 to about 30, or about 15 to about 30, or about 5 to about 25, or about 10 to about 25, and the like.

A polymeric macromolecule as a linking group may be a naturally-occurring material or a synthetic construct. In some embodiments the polymeric macromolecular linking group is a polypeptide. Examples of polypeptides, by way of illustration and not limitation, include proteins such as, e.g., albumins, gammaglobulins, immunoglobulins, hemocyanins, synthetic polypeptides, and the like. Examples of other polymeric macromolecules, by way of illustration and not limitation, include dendrimers, polymeric carboxylates (e.g., polyaspartic acid, polyglutamic acid, polygalacturonic acid, polymethacrylic acid, etc.), polymeric amines (e.g., polyethylene amine, polylysine, polyglutamine, polyethylene imine, polyallylamine, etc.), polymeric ethers (polyethyleneglycols or polyethylene oxide, etc.), polymeric thioethers (e.g., polyethylene thioethers, etc.), polymeric sulfhydryls (e.g. polycysteine) and so forth.

The binding partner for the analyte may be bound to a chemiluminescent composition in a number of different ways, some of which are discussed below by way of illustration and not limitation. In some embodiments the linking group is a protein and the components of the chemiluminescent composition, namely, an olefinic compound and a metal chelate, are each bound to the protein, to which a binding partner for the analyte is also bound. This embodiment is illustrated as follows:

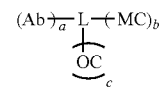

wherein Ab is a binding partner for the analyte (in this example, an antibody), L is protein linking group, MC is metal chelate and OC is olefinic compound and a, b and c are independently an integer of 1 to about 10, or 1 to about 9, or 1 to about 8, or 1 to about 7, or 1 to about 6, or 1 to about 5, or 1 to about 4, or 1 to about 3, or 1 to about 2, or 2 to about 10, or 2 to about 9, or 2 to about 8, or 2 to about 7, or 2 to about 6, or 2 to about 5, or 2 to about 4, or 2 to about 3, or about 3 to about 10, or about 3 to about 9, or about 3 to about 8, or about 3 to about 7, or about 3 to about 6, or about 3 to about 5, or about 3 to about 4, for example. Various functionalities such as amine, carboxyl and the like are present on the protein for linking to MC, OC and Ab and, as can be seen, multiple molecules of MC, OC and Ab may be bound to the protein. The number of molecules of each that may be bound is dependent on the size of the protein, the size of MC and OC and the size of the antibody.

In some embodiments the linking group is a protein and the components of the chemiluminescent composition, namely, an olefinic compound and a metal chelate, are each bound to the same molecule of the protein. The protein has one or more molecules of a member of a specific binding pair bound thereto. The binding partner for the analyte has one or more molecules of the other member of the specific binding pair bound thereto. The binding of the members of the specific binding pair results in the non-covalent binding of the binding partner for the analyte to the protein. This embodiment is illustrated as follows:

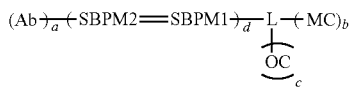

wherein Ab is a binding partner for the analyte (in this example, an antibody), L is protein linking group, MC is metal chelate, OC is olefinic compound, SBPM1 and SBPM2 are complementary members of a specific binding pair, = is a non-covalent bond, and a, b, c and d are independently an integer of 1 to about 10, or 1 to about 9, or 1 to about 8, or 1 to about 7, or 1 to about 6, or 1 to about 5, or 1 to about 4, or 1 to about 3, or 1 to about 2, or 2 to about 10, or 2 to about 9, or 2 to about 8, or 2 to about 7, or 2 to about 6, or 2 to about 5, or 2 to about 4, or 2 to about 3, or about 3 to about 10, or about 3 to about 9, or about 3 to about 8, or about 3 to about 7, or about 3 to about 6, or about 3 to about 5, or about 3 to about 4, for example. Various functionalities such as amine, carboxyl and the like are present on the protein for linking to MC, OC and SBPM1 and, as can be seen, multiple molecules of MC, OC and SBPM1 may be bound to the protein. The number of molecules of each that may be bound is dependent on the size of the protein, the size of MC, OC, SBPM1 and SBPM2 and the size of the antibody.

In some embodiments the linking group is a protein and the components of the chemiluminescent composition, namely, an olefinic compound and a metal chelate, are each bound to the same molecule of the protein. The protein has one or more molecules of a member of a specific binding pair bound thereto as well as one or more molecules of the antibody. OC and MC each independently have one or more molecules of the other member of the specific binding pair bound thereto. The binding of the members of the specific binding pair results in the non-covalent binding of OC and MC to the protein. This embodiment is illustrated as follows:

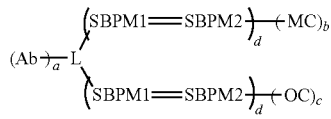

wherein Ab is a binding partner for the analyte (in this example, an antibody), L is protein linking group, MC is metal chelate, OC is olefinic compound, SBPM1 and SBPM2 are complementary members of a specific binding pair, = is a non-covalent bond, and a, b, c and d are independently an integer of 1 to about 10, or 1 to about 9, or 1 to about 8, or 1 to about 7, or 1 to about 6, or 1 to about 5, or 1 to about 4, or 1 to about 3, or 1 to about 2, or 2 to about 10, or 2 to about 9, or 2 to about 8, or 2 to about 7, or 2 to about 6, or 2 to about 5, or 2 to about 4, or 2 to about 3, or about 3 to about 10, or about 3 to about 9, or about 3 to about 8, or about 3 to about 7, or about 3 to about 6, or about 3 to about 5, or about 3 to about 4, for example. Various functionalities such as amine, carboxyl and the like are present on the protein for linking to MC, OC and SBPM1 and, as can be seen, multiple molecules of MC, OC and SBPM1 may be bound to the protein. The number of molecules of each that may be bound is dependent on the size of the protein, the size of MC, OC, SBPM1 and SBPM2 and the size of the antibody. It should be noted that in the above embodiment the specific binding pair to which SBPM1 and SBPM2 belong may be the same for attachment of OC and MC, or two different specific binding pairs may be employed, one for OC and one for MC.

In some embodiments the linking group is a protein and the components of the chemiluminescent composition, namely, an olefinic compound and a metal chelate, are each bound to the same molecule of the protein. The protein has one or more molecules of a member of a specific binding pair bound thereto. OC and MC each independently have one or more molecules of the other member of the specific binding pair bound thereto. The binding of the members of the specific binding pair results in the non-covalent binding of OC and MC to the protein. The binding partner for the analyte also has one or more molecules of the other member of the specific binding pair bound thereto. The binding of the members of the specific binding pair results in the non-covalent binding of the binding partner for the analyte to the protein. This embodiment is illustrated as follows:

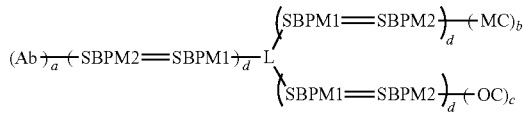

wherein Ab is a binding partner for the analyte (in this example, an antibody), L is protein linking group, MC is metal chelate, OC is olefinic compound, SBPM1 and SBPM2 are complementary members of a specific binding pair, = is a non-covalent bond, and a, b, c and d are independently an integer of 1 to about 10, or 1 to about 9, or 1 to about 8, or 1 to about 7, or 1 to about 6, or 1 to about 5, or 1 to about 4, or 1 to about 3, or 1 to about 2, or 2 to about 10, or 2 to about 9, or 2 to about 8, or 2 to about 7, or 2 to about 6, or 2 to about 5, or 2 to about 4, or 2 to about 3, or about 3 to about 10, or about 3 to about 9, or about 3 to about 8, or about 3 to about 7, or about 3 to about 6, or about 3 to about 5, or about 3 to about 4, for example. Various functionalities such as amine, carboxyl and the like are present on the protein for linking to SBPM1 and, as can be seen, multiple molecules of SBPM1 may be bound to the protein. The number of molecules of each that may be bound is dependent on the size of the protein, the size of MC, OC, SBPM1 and SBPM2 and the size of the antibody. It should be noted that in the above embodiment the specific binding pair to which SBPM1 and SBPM2 belong may be the same for attachment of OC, MC and the antibody or two or three different specific binding pairs may be employed, one for OC, one for MC and one for the antibody.

In some embodiments the linking group is a protein and the components of the chemiluminescent composition, namely, an olefinic compound and a metal chelate, are respectively bound to different molecules of the protein. The protein has one or more molecules of a member of a specific binding pair bound thereto. The binding partner for the analyte has one or more molecules of the other member of the specific binding pair bound thereto. The binding of the members of the specific binding pair results in the non-covalent binding of the binding partner for the analyte to the protein. This embodiment is illustrated as follows:

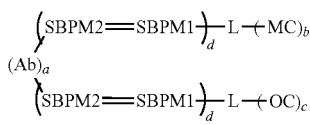

wherein Ab is a binding partner for the analyte (in this example, an antibody), L is protein linking group, MC is metal chelate, OC is olefinic compound, SBPM1 and SBPM2 are complementary members of a specific binding pair, = is a non-covalent bond, and a, b, c and d are independently an integer of 1 to about 10, or 1 to about 9, or 1 to about 8, or 1 to about 7, or 1 to about 6, or 1 to about 5, or 1 to about 4, or 1 to about 3, or 1 to about 2, or 2 to about 10, or 2 to about 9, or 2 to about 8, or 2 to about 7, or 2 to about 6, or 2 to about 5, or 2 to about 4, or 2 to about 3, or about 3 to about 10, or about 3 to about 9, or about 3 to about 8, or about 3 to about 7, or about 3 to about 6, or about 3 to about 5, or about 3 to about 4, for example. Various functionalities such as amine, carboxyl and the like are present on the protein for linking to MC, OC and SBPM1 and, as can be seen, multiple molecules of MC, OC and SBPM1 may be bound to the protein. The number of molecules of each that may be bound is dependent on the size of the protein, the size of MC, OC, SBPM1 and SBPM2 and the size of the antibody. It should be noted that in the above embodiment the specific binding pair to which SBPM1 and SBPM2 belong may be the same for attachment of OC and MC or two different specific binding pairs may be employed, one for OC and one for MC. It should also be noted that in the above embodiment L may be the same or different for OC and MC.

In some embodiments the linking group is a protein and the components of the chemiluminescent composition, namely, an olefinic compound and a metal chelate, are respectively bound to different molecules of the protein by means of non-covalent binding. The protein has one or more molecules of a member of a specific binding pair bound thereto. The binding partner for the analyte has one or more molecules of the other member of the specific binding pair bound thereto. The binding of the members of the specific binding pair results in the non-covalent binding of the binding partner for the analyte to the protein. OC and MC also each independently have one or more molecules of the other member of the specific binding pair bound thereto. The binding of the members of the specific binding pair results in the non-covalent binding of OC and MC to the protein. This embodiment is illustrated as follows:

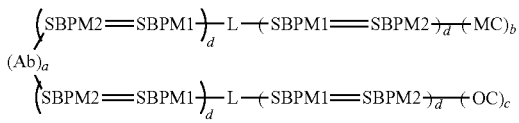

wherein Ab is a binding partner for the analyte (in this example, an antibody), L is protein linking group, MC is metal chelate, OC is olefinic compound, SBPM1 and SBPM2 are complementary members of a specific binding pair, = is a non-covalent bond, and a, b, c and d are independently an integer of 1 to about 10, or 1 to about 9, or 1 to about 8, or 1 to about 7, or 1 to about 6, or 1 to about 5, or 1 to about 4, or 1 to about 3, or 1 to about 2, or 2 to about 10, or 2 to about 9, or 2 to about 8, or 2 to about 7, or 2 to about 6, or 2 to about 5, or 2 to about 4, or 2 to about 3, or about 3 to about 10, or about 3 to about 9, or about 3 to about 8, or about 3 to about 7, or about 3 to about 6, or about 3 to about 5, or about 3 to about 4, for example. Various functionalities such as amine, carboxyl and the like are present on the protein for linking to MC, OC and SBPM1 and, as can be seen, multiple molecules of MC, OC and SBPM1 may be bound to the protein. The number of molecules of each that may be bound is dependent on the size of the protein, the size of MC, OC, SBPM1 and SBPM2 and the size of the antibody. It should be noted that in the above embodiment the specific binding pair to which SBPM1 and SBPM2 belong may be the same for attachment of OC, MC and antibody or two or three different specific binding pairs may be employed, one for OC and one for MC and one for the antibody. It should also be noted that in the above embodiment L may be the same or different for OC and MC.

The olefinic compound is one that is capable of reaction with singlet oxygen. In some embodiments, reaction of olefins with singlet oxygen is 2+2 addition to form a dioxetane. Suitable olefinic compounds usually have no saturated C—H group attached to an olefinic carbon except unreactive bridgehead carbons and, in some embodiments, have one or more electron donating groups directly attached to the olefinic carbon or in conjugation with the olefin. Dioxetanes can dissociate spontaneously or by heating with spontaneous chemiluminescence, or the carbonyl groups that are formed can be formed as part of a fluorescent group or be capable of undergoing subsequent reactions that lead to a fluorescent molecule. Alternatively, this dissociation reaction can lead to separation of a quenching group from a fundamentally fluorescent group that thereby regains its fluorescent property.

In some embodiments, reaction of singlet oxygen with olefins is 4+2 cycloaddition with dienes, usually aromatic compounds such as naphthalenes, anthracenes, oxazoles, furans, indoles, and the like. Such a reaction leads initially to an endoperoxide. In some cases endoperoxides can rearrange to active esters or anhydrides that are capable of reaction with a suitably placed group to provide a lactone or lactam that can be fluorescent. Alternatively, the endoperoxides may oxidize a fluorescent or chemiluminescent compound precursor. Endoperoxides can also dissociate spontaneously or on heating with chemiluminescent emission or oxidize a fluorescent leuco dye.

In some embodiments, reaction of singlet oxygen with olefins is the "ene" reaction that produces an allylhydroperoxide. Suitable olefins have a reactive saturated C—H attached to an olefinic carbon. This product can react with an active ester in the same molecule to form a dioxetanone that can spontaneously or by heating dissociate with chemiluminescent emission.

In general, olefins of interest are those that undergo a chemical reaction upon reaction with singlet oxygen to form a metastable reaction product, usually a dioxetane or endoperoxide, which is capable of decomposition with the simultaneous or subsequent emission of light, usually within the wavelength range of 250 to 1200 nm. Preferred are electron rich olefins usually containing electron-donating groups. Exemplary of such electron rich olefins are enol ethers, enamines, 9-alkylidene-N-alkylacridans, arylvinylethers, 1,4-dioxenes, 1,4-thioxenes, 1,4-oxazines, arylimidazoles, 9-alkylidene-xanthanes and lucigenin.

Examples of suitable electron rich chemiluminescent olefins are set forth in U.S. Pat. No. 5,709,994, the relevant disclosure of which is incorporated herein by reference. Such olefins generally have an electron-donating group in conjugation with the olefin.

The dioxetanes may be luminescent alone or in conjunction with a fluorescent energy acceptor. Enol ethers are examples of such olefins. In some embodiments, the enol ether compounds will have at least one aryl group bound to the olefinic carbons where the aryl ring is substituted with an electron donating group at a position that increases the reactivity of the olefin to singlet oxygen and/or imparts fluorescence to the product of dissociation of the resultant dioxetane. The electron-donating group can be, for example, hydroxyl, alkoxy, disubstituted amino, alkyl thio, furyl, pyryl, etc. Preferably, the enol ethers have an electron-donating group bound directly to an olefinic carbon.

Enamines are another example of such olefins. In general, useful enamines will be governed by the rules set forth above for enol ethers. Another family of chemiluminescers is the 2,4,5-triphenylimidazoles, with lophine as the common name for the parent product. Chemiluminescent analogs include para-dimethylamino and para-methoxy substituents. Other chemiluminescent olefins that satisfy the requirements given above may be found in European Patent Application No. 0,345,776.

In addition to the olefinic compound, the chemiluminescent composition comprises a complex of a metal and one or more chelating agents. Examples of metals that form part of the complex include, for example, rare earth metals, metals in Group VIII, and the like. The rare earth metals comprise the lanthanoids (lanthanide metals) (the 15 elements from lanthanum to lutetium, atomic numbers 57-71). The rare earth metals of particular interest include europium, terbium, dysprosium and samarium. The metals of Group VIII a particular interest include osmium and ruthenium. In some embodiments, rare earth metals have an oxidation state of plus three, ruthenium has an oxidation state of plus two and osmium has an oxidation state of plus two. In certain embodiments the metal is selected from the group consisting of europium, terbium, dysprosium, samarium, osmium and ruthenium. In some embodiments the metal is at least hexacoordinated; however, the metal may be octacoordinated or more highly coordinated depending on the metal chelating agent.

The metal chelating agent is a compound in which two or more atoms of the same molecule can coordinate with a metal to form a metal chelate. The two or more atoms may be, for example, oxygen, nitrogen, sulfur, and the like. The atoms may be in the form of one or more functionalities such as, for example, ketone, aldehyde, hydroxyl, amine, thioketone, thioaldehyde, thiol, and the like. The functionalities may be part of a benzyl group or a condensed aromatic ring system derived from, for example, naphthalene, anthracene, phenanthrene, acridine and so forth.

One of the aforementioned metals is coordinated with one or more chelating agents, particle examples of which include, for example, 2-(1',1',1',2',2',3',3'-heptafluoro-4',6'-hexanedion-6'-yl)-naphthalene (NHA), 4,4'-bis(2",3",3"-heptafluoro-4",6"-hexanedion-6"-yl)-o-terphenyl (BHHT), 4,4'-bis(1",1",1",2",2",3",3"-heptafluoro-4",6"-hexanedion-6"-yl)-chlorosulfo-o-terphenyl (BHHCT), phenanthroline (phen) and phenanthroline-related compounds (derivatives of phenanthroline) such as, e.g., phenanthroline carboxylic acid, 4,7-diphenyl-1,10-phenanthroline (DPP), and the like, 3-(2-thienoyl, 1,1,1-trifluoroacetone (TTA), thiophenetrifluorobutanedione (TTB), 3-naphthoyl-1,1,1-trifluoroacetone (NPPTA), naphthyltrifluorobutanedione (NTA), trioctyl phosphine oxide (TOPO), triphenyl phosphine oxide (TPPO). 3-benzoyl-1,1,1-trifluoroacetone (BFTA), 2,2-dimethyl-4-perfluorobutynoyl-3-butanone (fod), 2,2'-dipyridyl (bpy), salicylic acid, bipyridylcarboxylic acid, aza crown ethers trioctylphosphine oxide, aza cryptands, and so forth as well as combinations of the above. As mentioned above, in some embodiments the metal in the metal chelate is at least hexacoordinated. The metal chelate will be uncharged; thus, the number of acidic groups provided by the chelating agent will equal the oxidation state of the metal. Exemplary of particular metal chelates, by way of illustration and not limitation, include $Eu(BHHCT)_2DPP$, $Eu(TTA)_3DPP$, $Eu(NTA)_3DPP$, $Eu(NHA)_3DPP$, $Eu(BHHT)_2DPP$, and metal chelates as discussed in U.S. Pat. No. 6,916,667 (for example, columns 5-9) and U.S. Patent Application No. 20060270063 (column 3-4), the relevant disclosures of which are incorporated herein by reference, and so forth.

Many of the chelating agents and metal chelates are known in the art and many are commercially available. In general, metal chelates can be prepared from a metal chelating agent by combining a metal chloride with the desired ratio of molecules of metal chelating agent in an aqueous buffered solvent and sufficient base to take up hydrochloric acid that is produced during the reaction. For example, metal chelates can be prepared by a procedure such as that described by Shinha, A. P., "Fluorescences and laser action in rare earth chelates," Spectroscopy Inorganic Chemistry, Vol 2, (1971), 255-288.

The chemiluminescent reagent may include a group or functionality that imparts hydrophilicity or aqueous solubility, which increases wettability of solids with water and the solubility in aqueous systems of compounds to which it is bound. One or more of such functionality may be present on the olefinic compound or on the metal chelate or both. Such functional group or functionality can be a substituent having 1 to 50 or more atoms and can include a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Such a group or functionality may be introduced into the chelating agent by methods that are well-known in the art for introducing such groups or functionalities into compounds.

After preparation of the chemiluminescent reagent, the chemiluminescent reagent may be placed in a suitable medium for storage until used in an assay. In many embodiments the medium is an aqueous medium, usually an aqueous buffered medium. The aqueous medium may be solely water or may include from 0.1 to about 40 volume percent of a cosolvent such as, for example, an organic solvent, which may be an alcohol, ether, ester, amine, amide, and the like. The pH for the medium will usually be in the range of about 4 to about 11, or in the range of about 5 to about 10, or in the range of about 6.5 to about 9.5. Various buffers may be used to achieve the desired pH and maintain the pH. Illustrative buffers include borate, phosphate, carbonate, tris, barbital, PIPES, HEPES, IVIES, ACES, MOPS, BICINE, and the like. The particular buffer employed is not critical, but with a particular chemiluminescent reagent one or another buffer may be preferred. In some embodiments, the medium in which the chemiluminescent reagent is stored is substantially similar to, or the same as, the medium for an assay for an analyte where the chemiluminescent reagent is one of the assay reagents employed. The solubility of the chemiluminescent reagent in an aqueous medium at room temperature is, for example, at least 50%, or at least 55%, or at least 60%, or at least 65%, or at least 70%, or at least 75%, or at least 80%, or at least 85%, or at least 90%, or at least 95% (weight to volume).

In a specific embodiment of the above, by way of illustration and not limitation, the chemiluminescent reagent comprises a thioxene and Eu(BHHCT)$_2$DPP, both of which are covalently bound to BSA, to which a binding partner for an analyte is also bound.

A member of a specific binding pair ("sbp member") for use in the present embodiments for non-covalent linking is one of two different molecules, having an area on the surface or in a cavity which specifically binds to and is thereby defined as complementary with a particular spatial and polar organization of the other molecule. The specific binding pair for use in the present embodiments is selected from the group consisting of (i) small molecule and binding partner for the small molecule and (ii) large molecule and binding partner for the large molecule. In some embodiments, the small molecule has a molecular weight less than about 2000, or less than about 1500, or less than about 1000, or less than about 500, or less than about 400, or less than about 300, or the like. Examples of small molecule-binding partner for the small molecule pairs, by way of illustration and not limitation, include biotin-binding partner for biotin (e.g., avidin, streptavidin, antibody for biotin, etc.), digoxin-binding partner for digoxin (e.g., antibody for digoxin, etc.), fluorescein-binding partner for fluorescein (antibody for fluorescein, etc.), rhodamine-binding partner for rhodamine (e.g., antibody for rhodamine), peptide-binding partner for the peptide (antibody for the peptide, etc.), analyte-specific binding partners (e.g., intrinsic factor for B12, folate binding factor for folate) and so forth.

In some embodiments of a specific binding pair for use in the present embodiments, the molecular weight of the large molecule is greater than about 2,000, or greater than about 5,000, or greater than about 10,000, or greater than about 50,000, or greater than about 100,000, or greater than about 500,000, or greater than about 1,000,000, or greater than about 5,000,000 or greater than about 10,000,000, or the like. Examples of large molecule-binding partner for the large molecule pairs, by way of illustration and not limitation, include members of an immunological pair such as antigen-antibody, hormone-hormone receptors, nucleic acid duplexes, IgG-protein A, polynucleotide pairs such as DNA-DNA, DNA-RNA, other receptors and ligands, and the like.

The nature of the binding partner for the analyte is dependent primarily on the nature of the analyte. The binding partner for the analyte may be an antibody, a polynucleotide, an analyte-specific binding protein other than an antibody, and so forth. An antibody is an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

An analyte may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as a bacterium or a cell bearing a blood group antigen such as A, B, D, etc., or an HLA antigen or the analyte may be a microorganism, e.g., bacterium, fungus, protozoan, or virus.

The polyvalent ligand analytes may be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligand has a molecular weight of at least about 5,000, more usually at least about 10,000. In the poly(amino acid) category, the poly(amino acids) of interest may be from about 5,000 to 5,000,000 molecular weight, more usually from about 20,000 to 1,000,000 molecular weight; among the hormones of interest, the molecular weights will usually range from about 5,000 to 60,000 molecular weight.

The analyte may be a protein such as, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9, CA15.3 and CA125, tissue specific antigens, such as, e.g., alkaline phosphatase, myoglobin, CK-MB and calcitonin, and peptide hormones. Other analytes of interest are mucopolysaccharides and polysaccharides.

The monoepitopic ligand analytes will generally be from about 100 to 2,000 molecular weight, more usually from about 125 to about 1,000 molecular weight. The analytes include drugs (e.g., drugs of abuse, therapeutic drugs, etc.), metabolites, pesticides, pollutants, and the like. Representative drugs of abuse (including misused drugs), by way of example and not limitation, include (i) alkaloids such as morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g., phenobarbital and secobarbital, diphenylhydantoin, primidone, ethosuximide, and their metabolites; (iv) aminoalkylbenzenes, with alkyl chain of from 2 to 3 carbon atoms, which include the amphetamines; catecholamines, which include ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which include cannabinol and tetrahydrocannabinol; (viii) hormones such as thyroxine, cortisol, triiodothyronine, testosterone, estradiol, estrone, progesterone, (ix) tricyclic antidepressants, which include imipramine, desmethylimipramine, amitriptyline, nortriptyline, protriptyline, trimipramine, chlomipramine, doxepine, and desmethyldoxepin; and (x) anti-neoplastics, which include methotrexate; and the like.

General Description of Assays for an Analyte Utilizing the Present Reagents

Embodiments of the present invention have application to assays for the determination of an analyte. In general, in such assays the reagents comprise, among others, a binding partner for the analyte. A sample suspected of containing an analyte is combined in an assay medium with a binding partner for the analyte. A determination is made of the extent of binding between the analyte and the binding partner for the analyte. A chemiluminescent reagent in accordance with the present embodiments is employed as a label reagent in the detection of this binding event. The assay can be performed either without separation (homogeneous) or with separation (heterogeneous) of any of the assay components or products. Heterogeneous assays usually involve one or more separation steps and can be competitive or non-competitive.

Some known assays utilize a signal producing system (sps) that employs a particulate chemiluminescent reagent, which has a metal chelate associated with a support and has at least first and second sps members. The designation "first" and "second" is completely arbitrary and is not meant to suggest any order or ranking among the sps members or any order of addition of the sps members in the present methods. The sps members may be related in that activation of one member of the sps produces a product such as, e.g., light, which results in activation of another member of the sps. In some embodiments of known assays, the sps members comprise a sensitizer and a chemiluminescent composition where activation of the sensitizer results in a product that activates the chemiluminescent composition. The second sps member usually generates a detectable signal that relates to the amount of bound and/or unbound sps member, i.e. the amount of sps member bound or not bound to the analyte being detected or to an agent that reflects the amount of the analyte to be detected. In accordance with the present invention, the non-particulate chemiluminescent reagent in accordance with the present embodiments and described above may be employed in place of the particulate chemiluminescent reagent of the known methods.

In some embodiments of methods in accordance with the present embodiments, the first sps member is a sensitizer, such as, for example, a photosensitizer and the second sps member is the non-particulate chemiluminescent reagent of the present embodiments that is activated as a result of the activation of the first sps member. The sensitizer may be any moiety that upon activation produces a product that activates the chemiluminescent reagent, which in turn generates a detectable signal. In many embodiments the sensitizer is capable of generating singlet oxygen upon activation.

In some embodiments the sensitizer is a photosensitizer for generation of singlet oxygen usually by excitation with light. The photosensitizer can be photoactivatable (e.g., dyes and aromatic compounds) or chemi-activated (e.g., enzymes and metal salts). When excited by light the photosensitizer is usually a compound comprised of covalently bonded atoms, usually with multiple conjugated double or triple bonds. The compound should absorb light in the wavelength range of about 200 to about 1100 nm, or about 300 to about 1000 nm, or about 450 to about 950 nm, with an extinction coefficient at its absorbance maximum greater than about 500 $M^{-1}$ $cm^{-1}$, or at least about 5000 $M^{-1}$ $cm^{-1}$, or at least about 50,000 $M^{-1}$ $cm^{-1}$ at the excitation wavelength. Photosensitizers that are to be excited by light will be relatively photostable and will not react efficiently with singlet oxygen. Several structural features are present in most useful photosensitizers. Most photosensitizers have at least one and frequently three or more conjugated double or triple bonds held in a rigid, frequently aromatic structure. The photosensitizer usually contains at least one group that accelerates intersystem crossing such as a carbonyl or imine group or a heavy atom selected from rows 3-6 of the periodic table, especially iodine or bromine, or they may have extended aromatic structures. Typical photosensitizers include acetone, benzophenone, 9-thioxanthone, eosin, 9,10-dibromoanthracene, methylene blue, metallo-porphyrins, such as hematoporphyrin, phthalocyanines, chlorophylis, rose bengal, buckminsterfullerene, etc., and derivatives of these compounds having substituents of 1 to 50 atoms for rendering such compounds more lipophilic or more hydrophilic and/or as attaching groups for attachment, for example, to an sps member or an sbp member.

The photosensitizers useful in the above methods include other substances and compositions that can produce singlet oxygen with or, less preferably, without activation by an external light source. Thus, for example, molybdate salts and chloroperoxidase and myeloperoxidase plus bromide or chloride ion (Kanofsky, J. Biol. Chem. (1983) 259 5596) have been shown to catalyze the conversion of hydrogen peroxide to singlet oxygen and water. Also included within the scope of photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Examples of other photosensitizers that may be utilized are those set forth in U.S. Pat. Nos. 5,340,716 and 6,251,581, the relevant disclosures of which are incorporated herein by reference.

In a particular embodiment, the present invention has application in the induced luminescence immunoassay referred to in U.S. Pat. No. 5,340,716 (Ullman) entitled "Assay Method Utilizing Photoactivated Chemiluminescent Label" ("induced luminescence assay"), which disclosure is incorporated herein by reference. In one approach in accordance with the present embodiments, the assay uses a particle incorporating a photosensitizer and a non-particulate chemiluminescent reagent as described above. The binding partner for an analyte of the present chemiluminescent reagent binds to an analyte to form a complex, or binds to a second sbp member to form a complex, in relation to the presence of the analyte. If the analyte is present, the photosensitizer and the chemiluminescent compound come into close proximity by virtue of the binding, to the analyte, of the binding partner for the analyte on the photosensitizer particle and the binding partner for the analyte that is part of the non-particulate chemiluminescent reagent in accordance with the present embodiments. The photosensitizer generates singlet oxygen and activates the non-particulate chemiluminescent reagent when the two labels are in close proximity. The activated chemiluminescent reagent subsequently produces light. The amount of light produced is related to the amount of the complex formed, which in turn is related to the amount of analyte present.

In some embodiments of the induced luminescence assay, a photosensitizer particle is employed that is conjugated to avidin. A biotinylated binding partner for an analyte is also employed. A non-particulate chemiluminescent reagent in accordance with the present embodiments is employed as part of the detection system. The reaction medium is incubated to allow the photosensitizer particles to bind to the biotinylated binding partner for the analyte by virtue of the binding between avidin and biotin and to also allow the binding partner for the analyte that is part of the photosensitizer reagent and the binding partner for the analyte that is part of the non-particulate chemiluminescent reagent in accordance with the present embodiments to bind to the analyte. Then, the medium is irradiated with light to excite the photosensitizer, which is capable in its excited state of activating oxygen to a singlet state. Because the chemiluminescent reagent is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence and/or amount of the analyte.

The sample to be analyzed is one that is suspected of containing an analyte. The samples are preferably from humans or animals and include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum.

The sample can be prepared in any convenient medium. Conveniently, the sample may be prepared in an assay medium, which is discussed more fully herein. In some instances a pretreatment may be applied to the sample such as, for example, to lyse blood cells, and the like. Such pretreatment is usually performed in a medium that does not interfere subsequently with an assay. An aqueous medium is preferred for the pretreatment.

As discussed briefly above, the assays are normally carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the determination. Illustrative buffers include borate, phosphate, carbonate, tris, barbital, PIPES, HEPES, IVIES, ACES, MOPS, BICINE, and the like. The particular buffer employed is not critical, but in an individual assay one or another buffer may be preferred.

Various ancillary materials may be employed in the above methods. For example, in addition to buffers the medium may comprise stabilizers for the medium and for the reagents employed. In some embodiments, in addition to these additives, proteins may be included, such as albumins; organic solvents such as formamide; quaternary ammonium salts; polyanions such as dextran sulfate; binding enhancers, e.g., polyalkylene glycols; polysaccharides such as dextran, trehalose, or the like. The medium may also comprise agents for preventing the formation of blood clots. Such agents are well known in the art and include, for example, EDTA, EGTA, citrate, heparin, and the like. The medium may also comprise one or more preservatives as are known in the art such as, for example, sodium azide, neomycin sulfate, PROCLIN® 300, Streptomycin, and the like. Any of the above materials, if employed, is present in a concentration or amount sufficient to achieve the desired effect or function.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 24 hours, or about 1 second to about 6 hours, or about 2 seconds to about 1 hour, or about 1 to about 15 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., or from about 15 to about 40° C.

The concentration of the analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of the analyte present in the sample), the particular detection technique and the concentration of the analyte normally determine the concentrations of the various reagents.

The concentrations of the various reagents in the assay medium will generally be determined by the concentration range of interest of the analyte, the nature of the assay, and the like. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above.

As mentioned above, embodiments of the aforementioned assays employ a particulate photosensitizer reagent. The particle may be comprised of an organic or inorganic, solid or fluid, water insoluble material, which may be transparent or partially transparent. The particles generally have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chrome particles or latex particles.

Examination Step

In a next step of an assay method, the medium is examined for the presence of a complex comprising the analyte and the binding partner for the analyte. The presence and/or amount of the complex indicates the presence and/or amount of the analyte in the sample.

The phrase "measuring the amount of an analyte" refers to the quantitative, semiquantitative and qualitative determination of the analyte. Methods that are quantitative, semiquantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of the present invention. The terms "detecting" and "determining," as well as other common synonyms for measuring, are contemplated within the scope of the present invention.

In many embodiments the examination of the medium involves detection of a signal from the medium where the signal produced results from the involvement of the chemiluminescent composition in accordance with the present embodiments. The presence and/or amount of the signal is related to the presence and/or amount of the analyte in the sample. The particular mode of detection depends on the nature of the sps. As discussed above, there are numerous methods by which a label of an sps can produce a signal detectable by external means. Activation of a signal producing system depends on the nature of the signal producing system members. For an sps member that is a sensitizer that is activated by light, the sps member is irradiated with light. Other activation methods will be suggested to those skilled in the art in view of the disclosures herein.

When a photosensitizer is used, the photosensitizer serves to activate the chemiluminescent reagent when the medium containing the above reactants is irradiated. The medium is irradiated with light having a wavelength of sufficient energy to convert the photosensitizer to an excited state and render it capable of activating molecular oxygen to singlet oxygen. When bound to a binding partner for the analyte, the photosensitizer concentration may be very low, frequently about $10^{-6}$ to about $10^{-12}$ M or lower. Generally, for the above embodiments involving a photosensitizer, the medium is irradiated with light having a wavelength of about 300 to about 1200 nm, or about 450 to about 950, or about 550 to about 800 nm.

The period of irradiation will depend on the lifetime of the activated chemiluminescent composition of embodiments of the present chemiluminescent reagents and the light intensity and the desired emission intensity. For short-lived activated chemiluminescent compositions, the period may be less than a second, usually about a millisecond but may be as short as a microsecond where an intense flashlamp or laser is used. For longer-lived activated chemiluminescent compositions, the irradiation period can be longer and a less intense steady light source can be used. In general, the integrated light intensity over the period of irradiation should be sufficient to excite at least 0.1% of the photosensitizer molecules, preferably at least 30%, and, most preferably, every photosensitizer molecule will be excited at least once.

A helium-neon laser is an inexpensive light source for excitation at 632.6 nm. Photosensitizers that absorb light at this wavelength are compatible with the emission line of a helium-neon laser and are, therefore, particularly useful in the present methods in which photosensitizers are employed. Other light sources include, for example, other lasers such as Argon, YAG, He/Cd, and ruby; photodiodes; mercury, sodium and xenon vapor lamps; incandescent lamps such as tungsten and tungsten/halogen; and flashlamps.

Temperatures during measurements generally range from about 10° to about 70° C., or from about 20° to about 45° C., or about 20° to about 25° C. In one approach standard curves are formed using known concentrations of the analytes to be screened. As discussed above, calibrators and other controls may also be used.

The luminescence or light produced in any of the above approaches can be measured visually, photographically, actinometrically, spectrophotometrically or by any other convenient means to determine the amount thereof, which is related to the amount of analyte in the medium. The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, and the like. The presence and amount of signal detected is related to the presence and amount of the analyte present in a sample.

A helium-neon laser is an inexpensive light source for excitation at 632.6 nm. Photosensitizers that absorb light at this wavelength are compatible with the emission line of a helium-neon laser and are, therefore, particularly useful in the present methods in which photosensitizers are employed. Other light sources include, for example, other lasers such as Argon, YAG, He/Cd, and ruby; photodiodes; mercury, sodium and xenon vapor lamps; incandescent lamps such as tungsten and tungsten/halogen; and flashlamps.

Kits Comprising Reagents for Conducting Assays

The present chemiluminescent reagent and other reagents for conducting a particular assay may be present in a kit useful for conveniently performing an assay for the determination of an analyte. In some embodiments a kit comprises in packaged combination a biotin-binding partner for analyte conjugate, streptavidin-sensitizer particles and a non-particulate chemiluminescent reagent in accordance with the present embodiments wherein the binding partner for the analyte of the chemiluminescent reagent recognizes and binds to a different epitope on the analyte than the binding partner for the analyte that is part of the biotin-binding partner for the analyte conjugate. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional sbp members, ancillary reagents, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

The phrase "at least" as used herein means that the number of specified items may be equal to or greater than the number recited. The phrase "about" as used herein means that the number recited may differ by plus or minus 10%; for example, "about 5" means a range of 4.5 to 5.5. The designations "first" and "second" are used solely for the purpose of differentiating between two items such as, for example, "first sps member" and "second sps member," and are not meant to imply any sequence or order or importance to one item over another.

The following examples further describe the specific embodiments of the invention by way of illustration and not limitation and are intended to describe and not to limit the scope of the invention. Parts and percentages disclosed herein are by volume unless otherwise indicated.

EXAMPLES

Materials:

Testing was conducted using the DIMENSION® RxL analyzer, available from Siemens Healthcare Diagnostics Inc., Newark Del. The instrument was employed using induced luminescence immunoassay technology and was equipped with an appropriate reader.

Unless indicated otherwise, reagents were purchased from Sigma-Aldrich (Milwaukee, Wis.) and used as received unless mentioned otherwise. BHHCT was synthesized as described by Yuan J. and Matsumoto K. (Anal. Biochem. 1998, 70: 596-601). Anti-TSH antibody, a monoclonal antibody, was prepared by known somatic cell hybridization techniques; see, for example, Köhler and Milstein, *Nature* 265:495-497, 1975.

Purity of samples was analyzed by analytical thin layer chromatography (TLC) performed on Analtech Uniplate Silica Gel GF (0.25 mm) glass-backed plates using the specified solvent. TLC spots were visualized by ultraviolet light (short and/or long wave length) and/or iodine vapors. Flash chromatography was carried out on Whatman silica gel 60 Å (230-400 mesh). $^1$H-NMR spectra were recorded on a Bruker Ultrashiel™-400 (400 MHz) spectrometer. Chemical shifts are reported in parts per million (ppm, δ) relative to tetramethylsilane as internal reference. NMR abbreviations used are s (singlet), d (doublet), m (multiplet) and t (triplet).

Preparation of Compound II (FIG. 1):

N-methyl aniline (I) (25 g, 233.3 mmol) and ethyl 5-bromo-valerate (25 g, 119.6 mmol) were added to a 100 ml round bottom flask. The contents of the flask were heated with stirring at 100° C. for 16 hours. The reaction mixture was allowed to cool to room temperature and was poured into ethyl acetate (50 mL). The ethyl acetate solution was washed with 20% sodium hydroxide (3×50 mL); the combined sodium hydroxide solution was extracted back once with ethyl acetate (25 mL) and the remaining aqueous sodium hydroxide solution was discarded. The combined ethyl acetate extract was washed with water (10 mL) and dried over $MgSO_4$. The clear ethyl acetate solution was concentrated to dryness on a rotary evaporator. Residual oil so obtained was purified by distillation under high vacuum (130-134° C., 0.5 mm Hg) to yield 21 g of a colorless liquid compound II. $^1$H-NMR ($CDCl_3$) δ: 7.18 (m, 2H), 6.68 (m, 3H), 4.2 (q, J=8.0 Hz, 2H), 3.36 (t, J=8.0 Hz, 2H), 2.92 (s, 3H), 2.33 (t, J=8.0 Hz, 2H), 1.64 (m, 4H), 1.24 (t, J=8.0 Hz, 3H).

Preparation of Compound III (FIG. 1):

Phosphorus oxychloride ($POCl_3$; 5 g, 33 mmol) was added dropwise over a period of 10 minutes, through a dropping funnel, to stirred N,N-dimethyl formamide (DMF; 8.8 g, 120 mmol) at 0-4° C. After 10 minutes at 0-4° C., compound II (3.7 g, 15.96 mmol) was added rapidly in one portion. The vial used for compound II was rinsed with 1 ml of DMF and the DMF solution was added to the stirred reaction mixture, which was heated with stirring at 100° C. for 1 hour. The reaction mixture was allowed to cool to room temperature and poured slowly into an ice-water mixture. The aqueous phase was neutralized with 20% sodium hydroxide and extracted with ethyl acetate (3×50 mL). The combined ethyl acetate solution was washed with water (20 mL) and dried over $MgSO_4$. The clear organic solution was concentrated to dryness under reduced pressure. The resulting oily residue was purified by flash column chromatography using ethyl acetate/dichloromethane (9/1; v/v) to give 2.46 g of the compound III $^1$H-NMR ($CDCl_3$) δ: 9.72 (s, 1H), 7.18 (d, J=8.0 Hz, 2H), 6.68 (d, J=8.0 Hz, 2H), 4.22 (q, J=8.0 Hz, 2H), 3.40 (m, 2H), 3.05 (s, 3H), 2.35 (t, J=8.0 Hz, 2H), 1.65 (m, 4H), 1.25 (t, J=8.0 Hz, 3H).

Preparation of Compound IV (FIG. 1):

Potassium cyanide (1.0 g, 15.3 mmol) was added to a solution of compound III (2.46 g, 9.34 mmol) in 15 mL of 60% ethanol stirred in a nitrogen atmosphere. The mixture was heated under reflux for 15 minutes. Benzaldehyde (1.05 g) dissolved in 10 ml ethanol was added to the refluxed reaction mixture over a period of 45 minutes. After 15 minutes, the cooled reaction mixture was poured into ethyl acetate (30 mL). The aqueous phase was separated and extracted back with ethyl acetate (3×30 mL). The combined ethyl acetate solution was dried over $MgSO_4$ and the clear solution was concentrated to dryness under reduced pressure. Crude reaction mixture was dissolved in 10 ml of dry ethanol, mixed with 0.25 ml of trimethylsilyl chloride and stirred for 16 hr at room temperature. The reaction mixture was poured into a mixture of saturated sodium bicarbonate (120 mL) and dichloromethane (30 mL). The aqueous phase was separated and extracted with dichloromethane (2×30 mL). The combined organic phase was washed with saturated sodium bicarbonate (60 ml) and dried over $MgSO_4$. The clear organic solution was concentrated to dryness under reduced pressure. The oily residue was purified by flash column chromatography using ethyl acetate/hexane (1/5; v/v) to give 196 mg of the compound IV. $^1$H-NMR ($CDCl_3$) δ: 7.84 (d, J=8 Hz, 2H), 7.34 (m, 5H), 6.54 (d, J=8

Hz, 2H), 5.86 (d, J=4 Hz, 1H), 4.86 (d, J=4 Hz, 1H), 4.14 (q, J=8.0 Hz, 2H), 3.38 (t, J=8.0 Hz, 2H), 3.00 (s, 3H), 2.34 (t, J=8.0 Hz, 2H), 1.64 (m, 4H), 1.25 (t, J=8.0 Hz, 3H).

Preparation of Compound V (FIG. 1):

A stirred solution of compound IV (176 mg, 0.476 mmol) in 8 mL of dry toluene was mixed with thioethanol (0.28 ml, 312 mg, 4.0 mmol) and trimethylsilyl chloride (0.51 mL, 436 mg, 4.0 mmol). After heating under reflux for 24 hr, under nitrogen, the cooled reaction mixture was poured into saturated sodium bicarbonate (15 mL). The organic phase was separated and washed with saturated sodium bicarbonate (10 mL). The combined aqueous phase was extracted back with dichloromethane (3×30 mL) and the dichloromethane extract washed with water (20 mL). The combined dichloromethane solution was dried over $MgSO_4$, filtered and concentrated to dryness. The oily residue was purified by preparative thin layer chromatography using ethyl acetate/dichloromethane (5/95; v/v) to give 93 mg of the compound V. $^1$H-NMR ($CDCl_3$) δ: 7.20-7.04 (m, 7H), 6.50 (d, J=8.0 Hz, 2H), 4.48 (m, 2H), 4.12 (q, J=8.0 Hz, 2H), 3.28 (m, 2H), 3.20 (m, 2H), 2.87 (s, 3H), 2.32 (t, J=8.0 Hz, 2H), 1.60 (m, 4H), 1.25 (t, J=8.0 Hz, 3H).

Preparation of Compound VI (FIG. 1):

Sodium hydroxide (30 mg, 0.75 mmol) was added to a stirred solution of compound V (28 mg, 0.068 mmol) in MeOH (1 mL)-THF (2 ml)-water (0.5 mL). The reaction mixture was stirred at room temperature for 4 hr when TLC analysis showed absence of any starting product. The reaction mixture was mixed with 1.5 mL of water and the pH was adjusted to 3.0 by a slow addition of 1 N HCl. The reaction mixture was evaporated to dryness under vacuum. The oily residue was dissolved in dichloromethane (50 ml) and washed with 10 mL of water. The clear organic solution was dried over $MgSO_4$, filtered and concentrated to dryness to give 23.6 mg of the compound VI. FAB-MS (negative mode) m/z: 382 [(M-H)$^-$, 100]; $^1$H-NMR ($CD_3OD$) δ: 7.15-7.09 (m, 7H), 6.81 (d, J=8.0 Hz, 2H), 4.47 (m, 2H), 3.35 (m, 2H), 3.22 (m, 2H), 2.97 (s, 3H), 2.31 (t, J=8.0 Hz, 2H), 1.58 (m, 4H).

Synthesis of BSA-Coupled Thioxene Carboxylate:

The thioxene carboxylate VI (12.2 mg; 32 mmol) was dissolved in 0.5 mL DMF. The mixture was mixed with a 0.1 mL DMF solution of N-hydroxysuccinimide (NETS) (16 mg; 140 mmol) and a 0.1 mL DMF solution of dicyclohexyl carbodiimide (16 mg; 79 mmol). After stirring for 16 hr at ambient temperature, the organic reaction mixture was added slowly to a 5-mL solution of bovine serum albumin (BSA) (55 mg; 0.82 mmol) in 100 mM sodium phosphate-0.2 mM europium chloride, pH 7.60. After 4 hr, precipitated solid was separated by centrifugation and discarded. The clear solution was passed through a Sephadex G25 column (2.6×30 cm) equilibrated and eluted with 100 mM sodium bicarbonate-0.2 mM europium chloride, pH 8.20. Protein-containing fractions were combined. BSA-thioxene, thus obtained, was calculated to incorporate 31 thioxene residues per mole of the protein utilizing an extinction coefficient of $1.33\times10^4$ mole$^{-1}$ cm$^{-1}$ at 330 nm.

Preparation of Activated BSA-Thioxene:

A 12 mL solution of BSA-thioxene (2 mg/mL protein; 0.36 mmol) was mixed with 1.2 mL of a 10 mg/mL solution of sulfoSMPB (sulfosuccinimidyl [4-[-maleimidophenyl] butyrate]); 26.2 mmol). After 3 hr at ambient temperature, the protein solution was separated from excess reagents by passage through a Sephadex G25 column (2.6×30 cm) equilibrated and eluted with 100 mM sodium phosphate-200 µM europium chloride, pH 6.0.

Preparation of IgG-BSA-Thioxene:

Coupling of activated BSA-thioxene from above with reduced antibody was carried out by mixing a 3.0 mL solution of anti-TSH antibody (referred to as "IgG" in above conjugate) with 0.33 mL of a 100 mM solution of dithiothreitol in 100 mM sodium phosphate-5.0 mM EDTA, pH 6.0. After heating at 37° C. for one hour, the protein solution was passed through a Sephadex G25 column (1.6×30 cm) equilibrated and eluted with 100 mM sodium phosphate-200 µM europium chloride, pH 6.0. The reduced antibody was calculated to contain 7.2 moles of free sulfhydryls per mole of the protein. A 7.3 mL solution of this reduced antibody containing 19 mg protein (136 µmoles) was mixed with 28 mL of activated BSA-thioxene containing 31 mg protein (463 µmoles) and the reaction mixture concentrated to 3 mL after adjusting pH to 7.0. After 16 hr at 4° C., the reaction mixture was quenched with 50 µL of a 20 mg/mL aqueous solution of N-ethylmaleimide. The protein solution was then purified by gel filtration over an AcA-34 column (1.6×70 cm) equilibrated and eluted with 50 mM Hepes-300 mM NaCl-0.2% polyethyleneglycol (PEG8000)-0.2 mM europium chloride, pH 8.0. Fractions, corresponding to first protein peak eluted from the column, were pooled and stored in presence of 0.25 mg/mL of neomycin sulfate.

Reaction of IgG-BSA-Thioxene with BHHCT:

A 5 mL solution of the IgG-BSA-thioxene from above, containing about 1 mg/mL protein, was mixed with a 0.5 mL DMF solution of BHHCT containing 4.5 mg BHHCT. Reaction mixture was shaken at ambient temperature for 16 hr and centrifuged at 3000 rpm for 10 min, and the clear solution was passed through a Sephadex G50 column (2.6×30 cm) equilibrated and eluted with 50 mM Hepes-300 mM NaCl-0.2% polyethyleneglycol (PEG8000)-0.2 mM europium chloride, pH 8.0. Protein-containing fractions were pooled and stored in presence of 0.25 mg/mL neomycin sulfate to give IgG-BSA-(thioxene)(BHHCT).

Figures 2, 3:
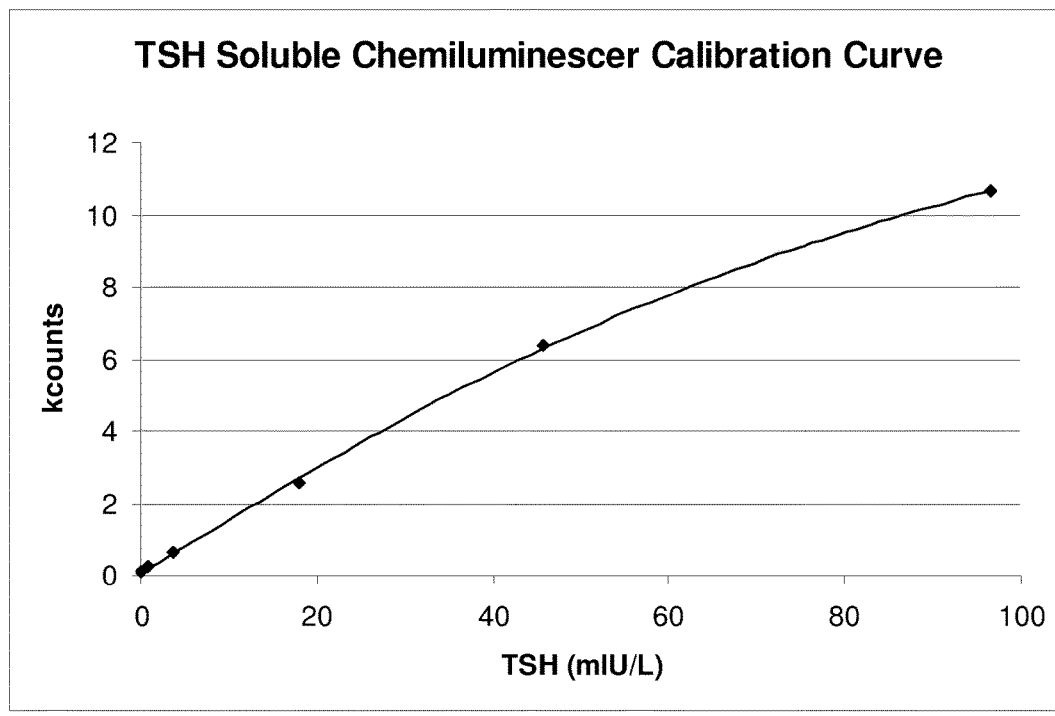
FIG. 2 is a graph depicting a calibration curve for an assay for TSH utilizing a chemiluminescent reagent in accordance with the present embodiments.
FIG. 3 is a tabular depiction of the results of an assay for TSH utilizing a chemiluminescent reagent in accordance with the present embodiments and showing the separation of signal obtained between calibrators.

Assay Utilizing IgG-BSA-(Thioxene)(BHHCT):

IgG-BSA-(thioxene)-(BHHCT) from above was diluted 1:100 in 50 mM HEPES buffer containing 0.2% PEG8000, 2 mg/mL BSA, 50 µM $EuCl_3$, 1 µM DPP, 0.15% PROCLIN300® and 0.2 mg/mL neomycin sulfate. In this manner, the BHHCT of the above reagent formed Eu(BHHCT)$_2$DPP in situ. The contents of wells 5-8 of a Dimension Vista® TSH FLEX® (Cat No. K6412, Lot 06229AB) were removed and the wells were rinsed with deionized water and re-filled with diluted reagent (IgG-BSA-(thioxene)-(Eu(BHHCT)$_2$DPP) from above. Wells containing biotinylated anti-TSH antibody (R1, wells 1-4) and streptavidin Sensibeads (photosensitizer beads) (R3, wells 9-12) were left intact. The 6-level LOCI® 1 Calibrator (Cat No. KC660, Lot 6BD036) was tested on VISTA® using this FLEX® and the VISTA® TSH method parameters (VISTA® Software 2.0). The calibration curve is shown in FIG. 2 wherein kcounts is kilocounts and TSH is thyroid stimulating hormone. The separation in LOCI® signal was 2.2-fold between level B and A, and 101-fold between level F and A. The N=3 within-run % CV ranged from 1.1% to 6.3% for calibrators B to F. The results are shown in FIG. 3.

Figure 4:
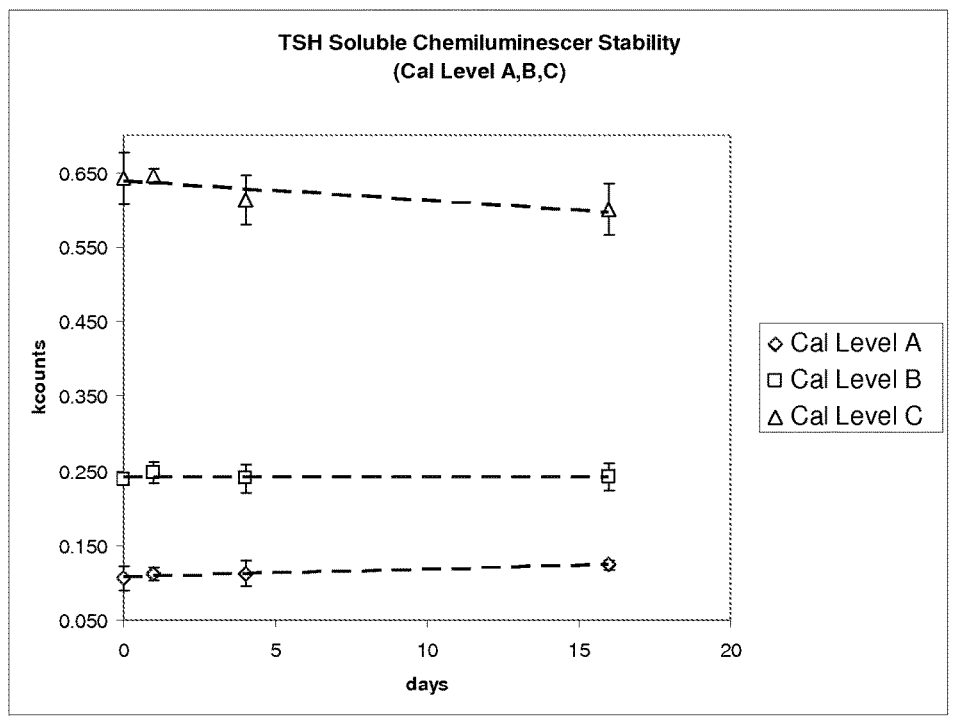
FIG. 4 is a graph depicting the results of a stability study of a chemiluminescent reagent in accordance with the present embodiments.
Figure 5:
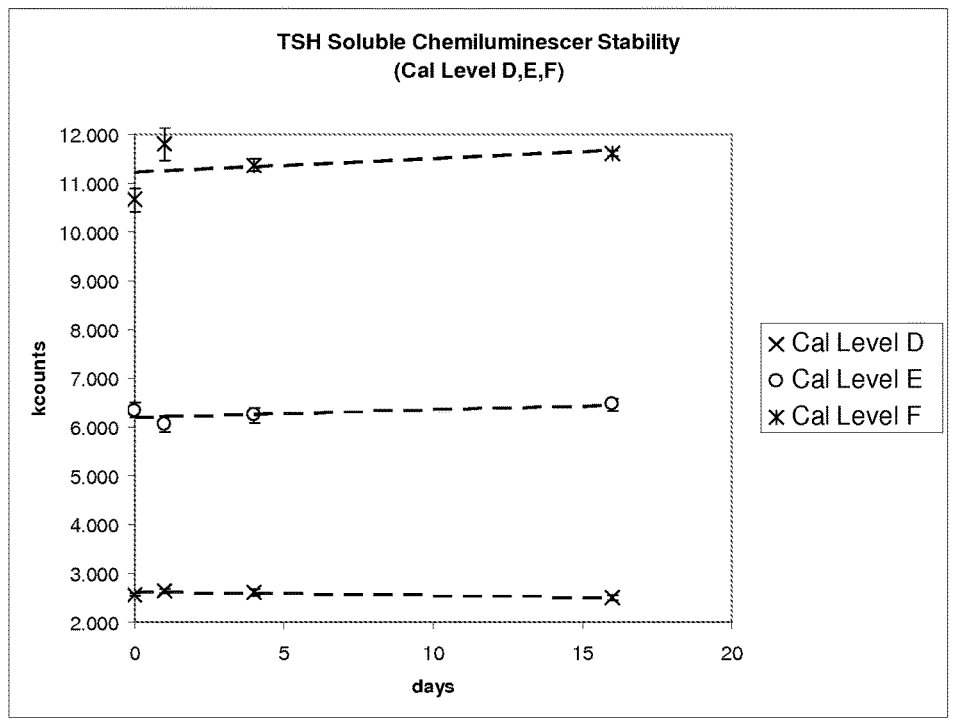
FIG. 5 is a graph depicting the results of a stability study of a chemiluminescent reagent in accordance with the present embodiments.

The FLEX® with the 1:100 diluted (IgG-BSA-(thioxene)-(Eu(BHHCT)$_2$DPP) was stored at 2-8° C. and tested periodically using LOCI® 1 Calibrator. Over a period of 16 days, the LOCI® signal for all non-zero calibrators (B to F) were within 10% of the day 0 value. The results are shown in FIGS. 4 and 5.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A chemiluminescent reagent for determining the presence and/or amount of an analyte in a sample suspected of containing the analyte, the reagent being non-particulate and soluble in an aqueous medium and comprising a binding partner for the analyte and a chemiluminescent composition comprising an olefinic compound and a metal chelate.

2. The chemiluminescent reagent according to claim 1 wherein the binding partner for the analyte is covalently bound to the chemiluminescent composition by a bond or a linking group.

3. The chemiluminescent reagent according to claim 2 wherein the binding partner for the analyte is covalently bound to the chemiluminescent composition by a linking group and wherein the linking group comprises a hydrophilic macromolecule.

4. The chemiluminescent reagent according to claim 3 wherein the olefinic compound and the metal chelate are linked to the same molecule of the linking group to which the binding partner for the analyte is covalently bound.

5. The chemiluminescent reagent according to claim 3 wherein the olefinic compound and the metal chelate are linked to separate molecules of the linking group to which the binding partner for the analyte is covalently bound and wherein the linking group may be the same or different.

6. The chemiluminescent reagent according to claim 3 wherein the hydrophilic macromolecule is selected from the group consisting of polypeptides, dendrimers, polycarboxylates, polyamines, polysulfhydryls and polyethyleneglycols.

7. The chemiluminescent reagent according to claim 1 wherein the binding partner for the analyte is non-covalently bound to the chemiluminescent composition by a specific binding pair wherein one member of the specific binding pair is linked to the binding partner for the analyte and the other member of the specific binding pair is linked to the chemiluminescent composition by a bond or a linking group.

8. The chemiluminescent reagent according to claim 7 wherein the binding partner for the analyte is non-covalently bound to the chemiluminescent composition by a specific binding pair wherein one member of the specific binding pair is linked to the binding partner for the analyte and the other member of the specific binding pair is linked to the chemiluminescent composition by a linking group wherein the linking group is a protein.

9. The chemiluminescent reagent according to claim 8 wherein the olefinic compound and the metal chelate are linked to the same molecule of the linking group to which the binding partner for the analyte is non-covalently bound.

10. The chemiluminescent reagent according to claim 8 wherein the olefinic compound and the metal chelate are linked to separate molecules of the linking group to which the binding partner for the analyte is non-covalently bound and wherein the linking group may be the same or different.

11. The chemiluminescent reagent according to claim 3 wherein the hydrophilic macromolecule is a protein.

12. The chemiluminescent reagent according to claim 7 wherein the specific binding pair is selected from the group consisting of (i) small molecule and binding partner for the small molecule and (ii) large molecule and binding partner for the large molecule.

13. The chemiluminescent reagent according to claim 1 wherein the metal of the metal chelate is a rare earth metal or a metal of Group VIII.

14. The chemiluminescent reagent according to claim 1 wherein the metal is selected from the group consisting of europium, terbium, dysprosium, samarium osmium and ruthenium.

15. The chemiluminescent reagent according to claim 1 wherein the metal chelate comprises a chelating agent selected from the group consisting of NHA, BHHT, BHHCT, DPP, TTA, NPPTA, NTA, TOPO, TPPO, BFTA, 2,2-dimethyl-4-perfluorobutyoyl-3-butanone (fod), 2,2'-dipyridyl (bpy), bipyridylcarboxylic acid, aza crown ethers, aza cryptands and trioctylphosphine oxide and derivatives thereof.

16. The chemiluminescent reagent according to claim 1 wherein the olefinic compound is selected from the group consisting of thioxenes, dioxenes, enol ethers, enamines, 9-alkylidenexanthans, 9-alkylidene-N-alkylacridans, aryl vinyl ethers, arylimidazoles and lucigenin and derivatives thereof.

17. The chemiluminescent reagent according to claim 1 wherein the metal is europium, the chelating agent is BHHCT and the olefinic compound is a carboxyl derivative of thioxene.

* * * * *